(12) United States Patent
Lee et al.

(10) Patent No.: US 9,109,097 B2
(45) Date of Patent: Aug. 18, 2015

(54) METHOD OF PREPARING SUPER ABSORBENT POLYMER

(71) Applicant: LG CHEM, LTD., Seoul (KR)

(72) Inventors: Yong Hun Lee, Daejeon (KR); Chang Sun Han, Daejeon (KR); Tae Young Won, Daejeon (KR); Dae Woo Nam, Daejeon (KR); Sung Soo Park, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/394,669

(22) PCT Filed: Dec. 16, 2013

(86) PCT No.: PCT/KR2013/011667
§ 371 (c)(1),
(2) Date: Oct. 15, 2014

(87) PCT Pub. No.: WO2014/112722
PCT Pub. Date: Jul. 24, 2014

(65) Prior Publication Data
US 2015/0094427 A1     Apr. 2, 2015

(30) Foreign Application Priority Data

Jan. 15, 2013 (KR) .................... 10-2013-0004455

(51) Int. Cl.
| | | |
|---|---|---|
| C08F 8/00 | (2006.01) | |
| C08J 3/24 | (2006.01) | |
| B01J 20/26 | (2006.01) | |
| A61F 13/53 | (2006.01) | |

(52) U.S. Cl.
CPC ............... C08J 3/245 (2013.01); A61F 13/53 (2013.01); B01J 20/26 (2013.01); B01J 20/267 (2013.01); C08J 3/24 (2013.01); *C08J 2333/02* (2013.01); *C08J 2433/00* (2013.01)

(58) Field of Classification Search
CPC ......... A61F 13/53; B01J 20/26; B01J 20/267; C08J 3/24; C08J 3/245; C08J 2333/02; C08J 2433/00
USPC ................................. 525/194, 197
See application file for complete search history.

(56) References Cited

U.S. PATENT DOCUMENTS

| | | | |
|---|---|---|---|
| 6,476,155 B1 | 11/2002 | Wada et al. | |
| 2011/0166300 A1* | 7/2011 | Dairoku et al. | 525/384 |
| 2013/0005919 A1* | 1/2013 | Kanzaki et al. | 525/384 |
| 2013/0026412 A1* | 1/2013 | Machida et al. | 252/194 |
| 2015/0099624 A1* | 4/2015 | Lee et al. | 502/402 |

FOREIGN PATENT DOCUMENTS

| | | |
|---|---|---|
| EP | 0819721 B1 | 8/2004 |
| JP | 56-161408 A | 12/1981 |
| JP | 57-198714 | 6/1982 |
| JP | 57-158209 A | 9/1982 |
| JP | 11-140194 A | 5/1995 |
| JP | 10-0449392 B1 | 2/2005 |
| JP | 2008-523173 A | 7/2008 |
| JP | 4583516 B2 | 10/2010 |
| KR | 0174745 B1 | 4/1991 |
| KR | 1998-701688 A | 6/1998 |
| KR | 1998-086055 A | 12/1998 |
| KR | 10-2011-0009580 A | 1/2011 |
| KR | 10-2011-0136597 A | 12/2011 |
| KR | 10-2012-0059169 A | 6/2012 |
| KR | 10-2012-0132475 A | 12/2012 |
| WO | 97-28209 A1 | 8/1997 |
| WO | 00-53664 A1 | 9/2000 |
| WO | 2006-101271 A1 | 9/2006 |
| WO | 2012-053121 A1 | 4/2012 |

* cited by examiner

*Primary Examiner* — Nathan M Nutter
(74) *Attorney, Agent, or Firm* — McKenna Long & Aldridge, LLP

(57) ABSTRACT

The present invention relates to a method of preparing a super absorbent polymer (SAP). The preparation method for SAP according to the present invention includes: preparing a first polymer by carrying out a thermal polymerization or photo polymerization of a monomer composition comprising a water-soluble ethylene-based unsaturated monomer and a polymerization initiator; preparing a second polymer by carrying out a thermal polymerization or photo polymerization of a monomer composition comprising a water-soluble ethylene-based unsaturated monomer and a polymerization initiator; drying the first polymer; milling the dried first polymer; and mixing the milled first polymer with the second polymer in the free swelling state using the crosslinking solution to cause a crosslinking reaction of the first and second polymers. According to the present invention, it is possible to obtain a super absorbent polymer (SAP) having high centrifuge retention capacity and high absorption under pressure.

10 Claims, No Drawings

METHOD OF PREPARING SUPER ABSORBENT POLYMER

This application is a 35 USC §371 National Stage entry of International Application No. PCT/KR2013/011667, filed on Dec. 16, 2013, and claims priority to Korean Application No. 10-2013-0004455, filed on Jan. 15, 2013, both of which are hereby incorporated by reference in their entireties as if fully set forth herein.

BACKGROUND OF THE INVENTION (a) Field of the Invention

The present invention relates to a method of preparing a super absorbent polymer. Particularly, the present invention relates to a method of preparing a super absorbent polymer having high centrifuge retention capacity and high permeability.

This application claims priority to Korea Patent Application No. 10-2013-0004455 filed on Jan. 15, 2013, and the contents are herein incorporated by reference.

(b) Description of the Related Art

Super absorbent polymer (SAP) is a synthetic polymer material having a function of absorbing water about five hundred times to about one thousand times the weight of itself, and it has been differently named as super absorbency material (SAM), absorbent gel material (AGM), and so on by developing companies. The SAP disclosed above started to be commercialized for sanitary items and is now widely used to water combination soil for horticulture, water-stop materials for civil engineering and construction, nursery sheets, freshness preservatives in the food distribution field, poultice materials, and the like, in addition to the sanitary fittings like paper diapers for babies.

An inverse suspension polymerization method or an aqueous polymerization method is known as a method of preparing super absorbent polymer. For example, the inverse suspension polymerization is disclosed in Japanese Patent Publication Nos. Sho56-161408, Sho57-158209, Sho57-198714, and so on. As the aqueous polymerization method, a thermal polymerization method polymerizing a hydrogel polymer while fracturing and cooling the same in a kneader equipped with a plurality of spindles, and a photo-polymerization method that exposes a high-concentrated aqueous solution on a belt to a UV ray and the like so as to carry out the polymerization and the dry at the same time are known.

Generally, the hydrogel polymer obtained by said polymerization reaction comes into the market in the form of powder after it is dried and milled.

On the other hand, there is a method of performing a polymerization and then a surface crosslinking reaction in order to obtain a super absorbent polymer with more excellent properties. Generally, the surface crosslinking reaction is accomplished by spraying a surface crosslinking solution obtained by adding a crosslinking agent to water on the surface of the polymer and, after agitation, applying a heat to cause the crosslinking reaction. With a view to controlling the penetration speed and depth of the surface crosslinking solution into the polymer particles, alcohols, polymers, or the like can be added to regulate the surface thickness of the polymer cross-linked.

The above-described method, however, leads to non-uniform application of the surface crosslinking solution on the surface of the super absorbent polymer and offers high permeability but a decrease in centrifuge retention capacity and absorption under pressure, ending up with the difficulty in acquiring satisfactory properties in all aspects.

SUMMARY OF THE INVENTION

For resolving the problems with the prior art, it is an object of the present invention to provide a method of preparing a super absorbent polymer (SAP) having properties enhanced through a uniform surface crosslinking reaction.

To achieve the object, the present invention provides a method of preparing a super absorbent polymer (SAP) that comprises:

preparing a first polymer by carrying out a thermal polymerization or photo polymerization of a monomer composition comprising a water-soluble ethylene-based unsaturated monomer and a polymerization initiator;

preparing a second polymer by carrying out a thermal polymerization or photo polymerization of a monomer composition comprising a water-soluble ethylene-based unsaturated monomer and a polymerization initiator;

drying the first polymer;

milling the dried first polymer; and mixing the milled first polymer with the second polymer in the free swelling state to cause a crosslinking reaction of the first and second polymers.

According to the preparation method for super absorbent polymer of the present invention, it is possible to prepare a super absorbent polymer having high centrifuge retention capacity and high permeability through a uniform crosslinking reaction.

According to the preparation method of the present invention, it is also possible to obtain a super absorbent polymer having high centrifuge retention capacity and high absorption under pressure without deterioration in the absorption under pressure and permeability.

DETAILED DESCRIPTION OF THE EMBODIMENTS

The method of preparing a super absorbent polymer (SAP) according to the present invention comprises: preparing a first polymer by carrying out a thermal polymerization or photo polymerization of a monomer composition comprising a water-soluble ethylene-based unsaturated monomer and a polymerization initiator; preparing a second polymer by carrying out a thermal polymerization or photo polymerization of a monomer composition comprising a water-soluble ethylene-based unsaturated monomer and a polymerization initiator; drying the first polymer; milling the dried first polymer; and mixing the milled first polymer with the second polymer in the free swelling state to cause a crosslinking reaction of the first and second polymers.

Since the present invention can be variously modified and have various examples, specific embodiments of the present invention are explained in this description. However, it is not intended to limit the present invention to the specific examples and it must be understood that the present invention includes every modifications, equivalents, or replacements included in the idea and technical scope of the present invention.

Hereinafter, a detailed description will be given as to a method of preparing a super absorbent polymer according to one embodiment of the present invention.

The method of preparing a super absorbent polymer (SAP) according to the present invention comprises: preparing a first polymer by carrying out a thermal polymerization or photo polymerization of a monomer composition comprising a water-soluble ethylene-based unsaturated monomer and a polymerization initiator; preparing a second polymer by carrying out a thermal polymerization or photo polymerization of a monomer composition comprising a water-soluble ethylene-based unsaturated monomer and a polymerization initiator; drying the first polymer; milling the dried first polymer; and mixing the milled first polymer with the second polymer in the free swelling state to cause a crosslinking reaction of the first and second polymers.

In the preparation method for super absorbent polymer according to the present invention, the first polymer is prepared by carrying out a thermal polymerization or photo polymerization of a monomer composition comprising a water-soluble ethylene-based unsaturated monomer and a polymerization initiator.

The monomer composition, which is a raw material for super absorbent polymer, comprises a water-soluble ethylene-based unsaturated monomer and a polymerization initiator.

As the water-soluble ethylene-based unsaturated monomer, any monomer generally used for the preparation of the SAP may be used unlimitedly. For example, the water-soluble ethylene-based unsaturated monomer may include at least one selected from the group consisting of an anionic monomer and a salt thereof, a nonionic hydrophilic monomer, and an unsaturated monomer containing amino group and a quaternary compound thereof.

More specifically, the water-soluble ethylene-based unsaturated monomer may include at least one selected from the group consisting of an anionic monomer, such as (meth)acrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid, and a salt thereof; a nonionic hydrophilic monomer, such as (meth)acrylamide, N-substituted (meth)acrylate, 2-hydroxyethyl(meth)acrylate, 2-hydroxypropyl(meth)acrylate, methoxypolyethyleneglycol(meth)acrylate, or polyethyleneglycol (meth)acrylate; and an unsaturated monomer containing amino group, such as (N,N)-dimethylaminoethyl(meth)acrylate or (N,N)-dimethylaminopropyl(meth)acrylate, and a quaternary compound thereof.

More preferably, the water-soluble ethylene-based unsaturated monomer may be an acrylic acid or a salt thereof, such as, for example, acrylic acid or an alkali metal salt thereof like sodium acrylate. The use of such a monomer enables it to prepare a super absorbent polymer with better properties. In the case of using the alkali metal salt of acrylic acid, acrylic acid can be used after neutralization with a basic compound such as sodium hydroxide (NaOH).

The concentration of the water-soluble ethylene-based unsaturated monomer may be about 20 to about 60 wt %, preferably about 40 to about 50 wt %, with respect to the monomer composition including the raw material of the SAP and the solvent, and it may be controlled to an adequate level in consideration of the polymerization time, reaction conditions, and so on. However, an extremely low concentration of the monomer leads to a low yield of the SAP and poor economic feasibility. On the contrary, an extremely high concentration of the monomer possibly causes problems with the process, such as having partial extraction of the monomer or low milling efficiency when milling the prepared hydrogel polymer, thereby deteriorating the properties of the SAP.

In the preparation method of the SAP of the present invention, the polymerization initiator used in the polymerization is not specifically limited so long as it is one generally used in the preparation of SAP.

More specifically, the polymerization initiator may be either a thermal polymerization initiator or a photo polymerization initiator using UV irradiation, depending on the polymerization method. However, even in the case of the photo polymerization method, a thermal polymerization initiator may be additionally used because a certain amount of heat is generated by the irradiation of UV ray and the like or by the progress of the polymerization reaction, which is an exothermic reaction.

The photo polymerization initiator is not specifically limited in its composition so long as it is a compound capable of forming a radical under a light such as UV rays.

The photo polymerization initiator, for example, may include at least one selected from the group consisting of benzoin ether, dialkyl acetophenone, hydroxyl alkylketone, phenyl glyoxylate, benzyl dimethyl ketal, acyl phosphine, and α-aminoketone. A specific example of acyl phosphine is lucirin TPO commercially available, namely, 2,4,6-trimethyl-benzoyl-trimethyl phosphine oxide. More examples of the photo polymerization initiator are well disclosed in "UV Coatings: Basics, Recent Developments and New Application" written by Reinhold Schwalm, (Elsevier, 2007), p 115. But, the photo polymerization initiator is not limited to those listed above.

The concentration of the photo polymerization initiator may be about 0.005 to about 1.0 wt % with respect to the monomer composition. When the concentration of the photo polymerization initiator is too low, the polymerization rate may become slow, and when the concentration of the photo polymerization initiator is too high, the molecular weight of the SAP becomes small and the properties may become uneven.

And, the thermal polymerization initiator may include at least one selected from the group consisting of a persulfate-based initiator, an azo-based initiator, hydrogen peroxide, and ascorbic acid. More specifically, examples of the persulfate-based initiator include sodium persulfate ($Na_2S_2O_8$), potassium persulfate ($K_2S_2O_8$), ammonium persulfate (($NH_4$)$_2$$S_2O_8$), etc.; and examples of the azo-based initiator include 2,2-azobis(2-amidinopropane)dihydrochloride, 2,2-azobis-(N,N-dimethylene)isobutyramidine dihydrochloride, 2-(carbamoylazo)isobutylonitril, 2,2-azobis[2-(2-imidazolin-2-yl) propane]dihydrochloride, 4,4-azobis-(4-cyanovaleric acid), etc. Other various thermal polymerization initiators are well disclosed in "Principle of Polymerization" written by Odian, (Wiley, 1981), p 203. But, the thermal polymerization initiator is not limited to those listed above.

The concentration of the thermal polymerization initiator may be about 0.001 to about 0.5 wt % with respect to the monomer composition. When the concentration of the thermal polymerization initiator is too low, the additional thermal polymerization hardly occurs and the effect of adding the thermal polymerization initiator may be poor, and when the concentration of the thermal polymerization initiator is too high, the molecular weight of the SAP becomes small and the properties may become uneven.

According to one embodiment of the present invention, the monomer composition may further include an internal crosslinking agent as a raw material of the SAP. The internal crosslinking agent may be a crosslinking agent having at least one ethylene-based unsaturated functional groups in addition to at least one functional group capable of reacting with the water-soluble substituents of the water-soluble ethylene-based unsaturated monomer; or a crosslinking agent having at least two functional groups capable of reacting with the water-soluble substituents of the monomer and/or the water-soluble substituents formed by hydrolysis of the monomer.

Specific examples of the internal crosslinking agent may include $C_8$-$C_{12}$ bisacrylamide, bismethacrylamide, poly (meth)acrylate of $C_2$-$C_{10}$ polyol, or poly(meth)allylether of $C_2$-$C_{10}$ polyol, etc. More specifically, the internal crosslinking agent may include at least one selected from the group consisting of N,N'-methylenebis(meth)acrylate, ethyleneoxy(meth)acrylate, polyethyleneoxy(meth)acrylate, propyleneoxy(meth)acrylate, glycerin diacrylate, glycerin triacrylate, trimethylol triacrylate, triallylamine, triarylcyanurate, triallylisocyanate, polyethyleneglycol, diethyleneglycol, and propyleneglycol.

Such an internal crosslinking agent may be included in the monomer composition at the concentration of about 0.001 to about 2.0 wt % to cross-link the prepared polymer.

In the preparation method of the present invention, the monomer composition of the SAP may further include additives, such as a thickener, a plasticizer, a shelf-life stabilizer, an antioxidant, and so on, under necessity.

The raw materials, such as the water-soluble ethylene-based unsaturated monomer, the photo polymerization initiator, the thermal polymerization initiator, the internal crosslinking agent, and the additives, can be prepared in the form of a solution of the monomer composition dissolved in a solvent.

In this regards, the solvent as used herein is not specifically limited in its composition so long as it can dissolve said components and may include, for example, at least selected from the group consisting of water, ethanol, ethyleneglycol, diethyleneglycol, triethyleneglycol, 1,4-butanediol, propyleneglycol, ethyleneglycol monobutylether, propyleneglycol monomethylether, propyleneglycol monomethylether acetate, methylethylketone, acetone, methylamylketone, cyclohexanone, cyclopentanone, diethyleneglycol monomethylether, diethyleneglycol ethylether, toluene, xylene, butylolactone, carbitol, methylcellosolve acetate, and N,N-dimethyl acetamide, which may be used alone or in combination.

The solvent may be included in the monomer composition in the residual quantity excluding the components disclosed above.

On the other hand, general method may be used without limitation so long as it can prepare a polymer from such monomer composition through thermal polymerization or photo polymerization.

Specifically, the polymerization method is largely classified into the thermal polymerization and the photo polymerization according to the polymerization energy source. Generally, the thermal polymerization may be carried out in a reactor like a kneader equipped with agitating spindles and the photo polymerization may be carried out in a reactor equipped with a movable conveyor belt. But, the above-described polymerization method is merely an example and may not limit the present invention.

For example, the hydrogel polymer obtained from the thermal polymerization in the reactor like kneader equipped with the agitating spindles disclosed above by providing hot air thereto or heating the reactor may have the size of several centimeters or millimeters when it is discharged from the outlet of the reactor, according to the type of the agitating spindles equipped in the reactor. Specifically, the size of the obtained hydrogel polymer can be variously shown according to the concentration of the monomer composition fed thereto, the feeding speed, and the like, and the hydrogel polymer having a weight average particle diameter of about 2 to 50 mm can be obtained.

Furthermore, in the case of the photo polymerization carried out with a reactor equipped with a movable conveyor belt disclosed above, the obtained hydrogel polymer may be a sheet type hydrogel polymer having the width same as the belt. In this regard, the thickness of the polymer sheet may vary according to the concentration of the monomer composition fed thereto and the feeding speed, and it is preferable to provide the monomer composition so that the sheet type hydrogel polymer has a width of about 0.5 to about 5 cm. It is not preferable that the monomer composition is fed so that the thickness of the sheet type polymer becomes too thin because the production efficiency is low. When the thickness of the sheet type polymer is larger than 5 cm, the polymerization reaction may not be occurred evenly throughout the whole thickness due to its excessively thick thickness.

According to one embodiment of the present invention, the moisture content of the first polymer obtained by such a method may be about 30 to about 60 wt % and preferably about 40 to about 55 wt %. Throughout the present specification, the term "moisture content" means the content of moisture with respect to the weight of whole hydrogel polymer, that is, the value obtained by subtracting the weight of the dried polymer from the weight of the hydrogel polymer. Specifically, the moisture content is defined as the value calculated by measuring the weight loss according to evaporation of water from the polymer during the dry process by elevating the temperature of the polymer through infrared heating. In this regard, the moisture content is measured by carrying out the dry process with the drying condition of elevating the temperature from room temperature to 180° C. and maintaining the temperature at 180° C., wherein the total drying time is set on 20 minutes including 5 minutes of temperature rising step.

Independently, the second hydrogel polymer is prepared by carrying out the thermal polymerization or photo polymerization of a monomer composition including a water-soluble ethylene-based unsaturated monomer and a polymerization initiator.

The details of the water-soluble ethylene-based unsaturated monomer, the polymerization initiator, the solvent, the internal crosslinking agent, and the additives used as the raw materials for the second polymer are as described in the preparation method of the first polymer disclosed above.

The second polymer of the present invention may be prepared by using the raw materials same as or different from those of the first polymer.

The second polymer of the present invention may have a moisture content of about 35 wt. % to 60 wt. %, preferably about 40 wt. % to about 55 wt. %, respectively.

The first or second polymer of the present invention may have a centrifuge retention capacity of about 25 g/g to about 60 g/g, as measured according to the EDANA WSP 241.2 method, respectively.

The first or second polymer of the present invention may have a water-soluble component content of about 5 wt. % to about 30 wt. %, as measured according to the EDANA WSP 270.2 method, respectively. The term "water-soluble component" as used herein refers to a polymer with low molecular weight that is soluble in water.

Subsequently, the first polymer thus obtained is dried out.

Under necessity, a coarse milling step may be further carried out before the drying step with a view to increasing the efficiency of the drying step.

The milling machine as used herein is not limited in its construction. Specifically, the milling machine may include, but is not limited to, at least one selected from the group consisting of a vertical pulverizer, a turbo cutter, a turbo grinder, a rotary cutter mill, a cutter mill, a disc mill, a shred crusher, a crusher, a chopper, and a disc cutter.

The milling step may be carried out so that the particle diameter of the first polymer is about 2 mm to about 10 mm.

It is technically not easy to coarse-mill the first polymer to have a particle diameter of less than 2 mm due to its high moisture content, and the coarse-milled particles may agglomerate when the particle diameter is less than 2 mm. When the particle diameter is greater than 10 mm, the increasing effect of the efficiency of the succeeding drying step can be insignificant The first polymer obtained immediately after the polymerization that is coarse-milled or not is dried out. In this regard, the drying temperature may be about 150° C. to about 250° C. When the drying temperature is lower than 150° C., there is a concern of that the drying time becomes excessively longer or the properties of the super absorbent polymer formed finally are deteriorated, and when the drying temperature is higher than 250° C., only the surface of the polymer is dried, and thus there is a concern of that fine powder may be generated and the properties of the super absorbent polymer formed finally are deteriorated. Hence, the drying temperature may be preferably in the range of about 150° C. to about 200° C., and more preferably about 160° C. to about 180° C.

The drying time may be about 20 minutes to about 90 minutes in consideration of the process efficiency, but it is not limited to or by this.

The drying method may be chose without limitation so long as it is generally used in the drying step for hydrogel polymer. Specifically, the drying step may be carried out by the method of supplying a hot air, irradiating an infrared ray, irradiating a microwave, or irradiating an ultraviolet ray, and the like. After the drying step disclosed above, the moisture content of the first polymer may be about 0.05 wt. % to about 5 wt %.

Subsequently, the dried first polymer obtained through the drying step is milled.

It is preferable that the particle diameter of the polymer powder obtained after the milling step is about 150 μm to about 850 μm. The milling device used for milling the polymer in such a particle diameter may include, but is not limited to, a pin mill, a hammer mill, a screw mill, a roll mill, a disc mill, a jog mill, and the like.

The milling step may generate a fine powder having a particle diameter less than about 150 μm.

In accordance with one embodiment of the present invention, the milled first polymer may be size-distributed into a fine powder having a particle diameter less than 150 μm and a polymer having a particle diameter of 150 to 850 μm. In addition, for reusing the fine powder having a particle diameter less than 150 μm, the reassembling process may be carried out to aggregate the fine powder.

Subsequently, the first and second polymers are subjected to a crosslinking reaction by mixing the first polymer with the second polymer in the free swelling state using a crosslinking agent.

In regards to the crosslinking density in the inside and on the surface of the polymer particles, the crosslinking reaction is a process to increase the crosslinking density of the SAP particles. This reaction may occur in the whole of the particles, including the inside and the surface of the SAP particles.

The crosslinking agent is used in the form of a crosslinking solution in water and applied to the surface of the SAP particles.

In many cases, however, the crosslinking solution is not uniformly applied to the surface of the SAP, or the crosslinking agent is dispersed not uniformly, in which cases the crosslinking reaction hardly occurs. Moreover, alcohols or polymers added to control the penetration rate and penetration depth of the crosslinking solution act as impurities that cause a foul odor or color change of the SAP. This ultimately brings about deterioration in the properties of the SAP powder obtained as the final product.

According to the preparation method of the present invention, the crosslinking reaction is conducted on the first and second polymers by mixing the first polymer with the second polymer in the free swelling state using the crosslinking solution rather than by directly adding the crosslinking agent. The term "free swelling" as used herein refers to the state that the second polymer absorbs the crosslinking solution without a restrained load and swollen.

In order to put the second polymer in the free swelling state using the crosslinking solution, the crosslinking solution may be added to the second polymer in the hydrogel form. Alternatively, the second polymer in the hydrogel form obtained by the polymerization process is dried, and then the crosslinking solution is applied to the dried second polymer to make the second polymer in the free swelling state. In addition, after the second polymer is dried, there may be further carried out a step of milling or size-distributing the second polymer to have an appropriate particle size before the crosslinking solution is added to make the second polymer in the free swelling state.

The second polymer in the free swelling state using the crosslinking solution may include the crosslinking solution having a weight about 0.5 to 500 times the total weight of the second polymer.

The second polymer in the free swelling state using the crosslinking solution serves as a medium for transferring the crosslinking solution uniformly to the surface of the first polymer. The second polymer in the free swelling state using the crosslinking solution is uniformly mixed with the first polymer. By this, the crosslinking solution can penetrate into the first polymer more uniformly than by adding the crosslinking solution in the form of an aqueous solution to cause a crosslinking reaction. Further, the second polymer absorbs the crosslinking solution and undergoes a crosslinking reaction while it is swollen, so it not only acts as a medium for transferring the crosslinking agent to the first polymer but also has a crosslinking reaction even in itself and on its surface with the remaining crosslinking agent.

It is therefore possible to form a SAP with a more uniform surface crosslinking thickness, consequently with excellent properties regarding centrifuge retention capacity, absorption under pressure, and permeability.

According to one embodiment of the present invention, the second polymer in the free swelling state using the crosslinking solution may be mixed in an amount of about 1 to 20 parts by weight with respect to 100 parts by weight of the first polymer.

The crosslinking solution comprises a crosslinking agent and water.

In this regard, the crosslinking agent is not limited in its composition so long as it is a compound capable of reacting with the functional group of the first polymer.

Preferably, with a view to enhancing the properties of the SAP prepared, the crosslinking agent may include at least one selected from the group consisting of a polyhydric alcohol compound; an epoxy compound; a polyamine compound; a haloepoxy compound; a condensation product of the haloepoxy compound; an oxazoline compound; a mono-, di-, or polyoxazolidinone compound; a cyclic urea compound; a polyvalent metal salt; and an alkylene carbonate compound.

Specifically, examples of the polyhydric alcohol compound may include at least one selected from the group consisting of mono-, di-, tri-, tetra- or polyethylene glycol, monopropylene glycol, 1,3-propanediol, dipropylene glycol, 2,3, 4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexane dimethanol.

Examples of the epoxy compound may include ethylene glycol diglycidyl ether, glycidol, etc. Examples of the polyamine compound may include at least one selected from the group consisting of ethylene diamine, diethylene triamine, triethylene triamine, tetraethylene pentamine, pentaethylene hexamine, polyethylene amine, and polyamide polyamine.

Examples of the haloepoxy compound may include epichlorohydrin, epibromohydrin, and α-methylephichlorohydrin. Examples of the mono-, di- or polyoxazolidinone compound may include 2-oxazolidinone, etc.

And, examples of the alkylene carbonate compound may include ethylene carbonate, etc. These compounds may be used alone or in combination. These compounds may be used solely or by combination. To enhance the efficiency of the surface crosslinking process, the crosslinking agent is preferably at least one polyhydric alcohol compound, more preferably at least one $C_2$-$C_{10}$ polyhydric alcohol compound.

According to one embodiment of the present invention, the crosslinking solution may further comprise porous silica, clay, or the like in order to enhance the permeability. Also, the crosslinking solution may further comprise an acidic compound, a polymer, or the like upon necessity in order to control the penetration rate and depth of the crosslinking agent.

The amount of the surface crosslinking agent in the crosslinking solution may be regulated depending on the type of the surface crosslinking agent or the reaction conditions and normally in the range of about 0.01 to 3 parts by weight, preferably about 0.05 to 2 parts by weight, with respect to 100 parts by weight of the first and second polymers in total.

When the content of the crosslinking agent is extremely small, less than 0.01 part by weight, the surface crosslinking reaction hardly occurs; and when the content of the crosslinking agent is greater than 3 parts by weight, an excessive progress of the surface crosslinking reaction occurs to cause deterioration in the centrifuge retention capacity and the properties.

The weight ratio of the crosslinking agent to water included in the crosslinking solution may range from about 1:1 to about 1:10.

The crosslinking reaction the drying process may be carried out simultaneously by heating the first polymer particles and the second polymer in the free swelling state using the crosslinking solution at an appropriate temperature. During the crosslinking reaction, the temperature may range from about 100° C. to about 250° C., preferably from about 130° C. to about 210° C.

The temperature elevating means for the surface crosslinking reaction is not specifically limited and may include applying a heat transfer medium or directly applying a heat source. In this regard, examples of the heat transfer medium as used herein may include, but are not limited to, any heated fluid, such as steam, hot air, or hot oil. And, the temperature of the heat transfer medium may be properly regulated in consideration of the means for the heat transfer medium, the heating rate, and the desired heating temperature. Examples of the heat source directly provided may include, but are not limited to, electricity or gas.

Generally, the SAP with high permeability tends to have a low centrifuge retention capacity and a low absorption under pressure. In other words, when the crosslinking density and the strength of the SAP are high, the permeability is high, but it is difficult to increase all of the centrifuge retention capacity, the absorption under pressure, and the permeability at the same time. However, the SAP obtained by the method of the present invention has high permeability as well as high centrifuge retention capacity and high absorption under pressure. What this result comes down to is the fact that the second polymer absorbing the crosslinking solution is mixed with the first polymer, which prevents the crosslinking agent from penetrating locally into the first polymer particles and thus induces forming a uniform coating of the crosslinking agent to cause a crosslinking reaction evenly on the surface of the first polymer particles. This can lead to high permeability without deterioration in the centrifuge retention capacity and the absorption under pressure.

The SAP obtained according to the preparation method of the present invention may have a centrifuge retention capacity ranging from about 20 g/g to about 55 g/g, preferably from about 25 g/g to about 50 g/g. Further, the SAP obtained according to the preparation method of the present invention may have a permeability ranging from about 15 seconds to about 150 seconds, preferably from about 30 seconds to about 100 seconds.

Hereinafter, the present invention is explained in more detail through the following examples. However, the following examples are only for illustrating the present invention and not intended to limit the scope of the present invention.

EXAMPLES

Preparation Example 1

500 g of acrylic acid and 2.5 g of ethoxylated (15) trimethylolpropane triacrylate were dissolved in a 3 L-glass container equipped with a stirrer, a nitrogen feeder, and a thermocouple. Then, 896.4 g of 24.5% sodium hydroxide solution was added while nitrogen was continuously fed, to prepare an aqueous solution of the water-soluble unsaturated monomer. The aqueous solution of the water-soluble unsaturated monomer was put in a 5 L twin-arm kneader with sigma-shaped spindles, and nitrogen was added for 30 minutes while the temperature was maintained at 75° C., thereby eliminating oxygen dissolved in the aqueous solution. Under agitation, to the resultant aqueous solution were added 40 g of a 0.3% aqueous solution of L-ascorbic acid and 40 g of an aqueous solution containing 1.25 g of potassium persulfate and 3.0 g of hydrogen peroxide in 100 g of water.

With the progress of the polymerization, a gel-type resin was formed and, under agitation for 30 minutes, divided to form a microgel-type hydrogel polymer. The moisture content of the hydrogel polymer thus obtained was 40.5%.

The hydrogel polymer was spread on a stainless wire gauze having a hole size of 600 μm to a thickness of about 30 mm and dried in a hot air oven at 170° C. for 5 hours. The dried polymer was milled by using a milling machine and then size-distributed through a standard sieve according to the ASTM standards to obtain a base resin having a particle size of 150 to 850 μm and a fine powder having a particle diameter of less than 150 μm. The yield of the fine powder was 15 wt. % with respect to the dried polymer.

The base resin had a centrifuge retention capacity of 40.5 g/g and a water-soluble component content of 11.4%.

Preparation Example 2

500 g of acrylic acid and 0.5 g of 1,6-hexadiol diacrylate (HDDA) were dissolved in a 3 L-glass container equipped with a stirrer, a nitrogen feeder, and a thermocouple. Then, 896.4 g of 24.5% sodium hydroxide solution was added while nitrogen is continuously fed, to prepare an aqueous solution of the water-soluble unsaturated monomer. The aqueous solution of the water-soluble unsaturated monomer was put in a 5 L twin-arm kneader with sigma-shaped spindles, and nitrogen was added for 30 minutes while the temperature was maintained at 85° C., thereby eliminating oxygen dissolved in the aqueous solution. Under agitation, to the resultant aqueous solution were added 40 g of a 0.3% aqueous solution of L-ascorbic acid and 40 g of an aqueous solution containing 5.0 g of potassium persulfate and 3.0 g of hydrogen peroxide in 100 g of water.

With the progress of the polymerization, a gel-type resin was formed and, under agitation for 30 minutes, divided to form a microgel-type hydrogel polymer. The moisture content of the hydrogel polymer thus obtained was 40.1%.

The hydrogel polymer was spread on a stainless wire gauze having a hole size of 600 μm to a thickness of about 30 mm and dried in a hot air oven at 180° C. for 5 hours. The dried polymer was milled by using a milling machine and then size-distributed through a standard sieve according to the ASTM standards to obtain a base resin having a particle size of 150 to 850 μm and a fine powder having a particle diameter of less than 150 μm. The yield of the fine powder was 15 wt. % with respect to the dried polymer.

The base resin had a centrifuge retention capacity of 50.1 g/g and a water-soluble component content of 21.4%.

Preparation Example 3

500 g of acrylic acid and 3.75 g of ethoxylated (15) trimethylolpropane triacrylate were dissolved in a 3 L-glass container equipped with a stirrer, a nitrogen feeder, and a thermocouple. Then, 896.4 g of 24.5% sodium hydroxide solution was added while nitrogen is continuously fed, to prepare an aqueous solution of the water-soluble unsaturated monomer. The aqueous solution of the water-soluble unsaturated monomer was put in a 5 L twin-arm kneader with sigma-shaped spindles, and nitrogen was added for 30 minutes while the temperature was maintained at 75° C., thereby eliminating oxygen dissolved in the aqueous solution. Under agitation, to the resultant aqueous solution were added 20 g of a 0.3% aqueous solution of L-ascorbic acid and 30 g of an aqueous solution containing 1.25 g of potassium persulfate and 3.0 g of hydrogen peroxide in 100 g of water.

With the progress of the polymerization, a gel-type resin was formed and, under agitation for 30 minutes, divided to form a microgel-type hydrogel polymer. The moisture content of the hydrogel polymer thus obtained was 40.2%.

The hydrogel polymer was spread on a stainless wire gauze having a hole size of 600 μm to a thickness of about 30 mm and dried in a hot air oven at 160° C. for 5 hours. The dried polymer was milled by using a milling machine and then size-distributed through a standard sieve according to the ASTM standards to obtain a base resin having a particle size of 150 to 850 μm and a fine powder having a particle diameter of less than 150 μm. The yield of the fine powder was 15 wt. % with respect to the dried polymer.

The base resin had a centrifuge retention capacity of 36.2 g/g and a water-soluble component content of 7.3%.

Preparation Example 4

500 g of acrylic acid and 1.5 g of 1,6-hexadiol diacrylate (HDDA) were dissolved in a 3 L-glass container equipped with a stirrer, a nitrogen feeder, and a thermocouple. Then, 896.4 g of 24.5% sodium hydroxide solution was added while nitrogen is continuously fed, to prepare an aqueous solution of the water-soluble unsaturated monomer. The aqueous solution of the water-soluble unsaturated monomer was put in a 5 L twin-arm kneader with sigma-shaped spindles, and nitrogen was added for 30 minutes while the temperature was maintained at 75° C., thereby eliminating oxygen dissolved in the aqueous solution. Under agitation, to the resultant aqueous solution were added 20 g of a 0.3% aqueous solution of L-ascorbic acid and 30 g of an aqueous solution containing 5.0 g of potassium persulfate and 3.0 g of hydrogen peroxide in 100 g of water.

With the progress of the polymerization, a gel-type resin was formed and, under agitation for 30 minutes, divided to form a microgel-type hydrogel polymer. The moisture content of the hydrogel polymer thus obtained was 40.1%.

The hydrogel polymer was spread on a stainless wire gauze having a hole size of 600 μm to a thickness of about 30 mm and dried in a hot air oven at 160° C. for 5 hours. The dried polymer was milled by using a milling machine and then size-distributed through a standard sieve according to the ASTM standards to obtain a base resin having a particle size of 150 to 850 μm and a fine powder having a particle diameter of less than 150 μm. The yield of the fine powder was 15 wt. % with respect to the dried polymer.

The base resin had a centrifuge retention capacity of 38.5 g/g and a water-soluble component content of 14.6%.

Preparation Example 5

500 g of acrylic acid, 2.25 g of ethoxylated (15) trimethylolpropane triacrylate and 0.165 g of diphenyl (2,4,5-trimethylbenzoyl)-phosphine oxide were dissolved in a 3 L-glass container equipped with a stirrer, a nitrogen feeder, and a thermocouple. Then, 896.4 g of 24.5% sodium hydroxide solution was added while nitrogen is continuously fed, to prepare an aqueous solution of the water-soluble unsaturated monomer. The aqueous solution of the water-soluble unsaturated monomer was cooled down to 50° C.

The resultant aqueous solution was put in a stainless container (250 mm×250 mm×30 mm) and exposed to UV radiation (exposure dose: 10 mW/cm$^2$) to conduct a UV polymerization for 90 seconds and obtain a hydrogel polymer. The hydrogel polymer thus obtained was milled to a size of 2 mm×2mm and measured in regards to the moisture content, which was 39.5%.

The hydrogel polymer was spread on a stainless wire gauze having a hole size of 600 μm to a thickness of about 30 mm and dried in a hot air oven at 160° C. for 5 hours. The dried polymer was milled by using a milling machine and then size-distributed through a standard sieve according to the ASTM standards to obtain a base resin having a particle size of 150 to 850 μm and a fine powder having a particle diameter of less than 150 μm. The yield of the fine powder was 15 wt. % with respect to the dried polymer.

The base resin had a centrifuge retention capacity of 40.2 g/g and a water-soluble component content of 11.8%.

Preparation Example 6

500 g of acrylic acid, 0.45 g of 1,6-hexadiol diacrylate (HDDA) and 0.04 g of diphenyl (2,4,6-trimethylbenzoyl)-phosphine oxide were dissolved in a 3 L-glass container equipped with a stirrer, a nitrogen feeder, and a thermocouple. Then, 896.4 g of 24.5% sodium hydroxide solution was added while nitrogen is continuously fed, to prepare an aqueous solution of the water-soluble unsaturated monomer. The aqueous solution of the water-soluble unsaturated monomer was cooled down to 70° C.

The resultant aqueous solution was put in a stainless container (250 mm×250 mm×30 mm) and exposed to UV radiation (exposure dose: 10 mW/cm$^2$) to conduct a UV polymerization for 90 seconds and obtain a hydrogel polymer. The hydrogel polymer thus obtained was milled to a size of 2 mm×2 mm and measured in regards to the moisture content, which was 39.7%.

The hydrogel polymer was spread on a stainless wire gauze having a hole size of 600 μm to a thickness of about 30 mm and dried in a hot air oven at 180° C. for 5 hours. The dried polymer was milled by using a milling machine and then size-distributed through a standard sieve according to the ASTM standards to obtain a base resin having a particle size of 150 to 850 μm and a fine powder having a particle diameter of less than 150 μm. The yield of the fine powder was 15 wt. % with respect to the dried polymer.

The base resin had a centrifuge retention capacity of 50.9 g/g and a water-soluble component content of 16.8%.

Preparation Example 7

500 g of acrylic acid, 2.25 g of ethoxylated (15) trimethylolpropane triacrylate and 0.04 g of diphenyl (2,4,6-trimethylbenzoyl)-phosphine oxide were dissolved in a 3 L-glass container equipped with a stirrer, a nitrogen feeder, and a thermocouple. Then, 896.4 g of 24.5% sodium hydroxide solution was added while nitrogen is continuously fed, to prepare an aqueous solution of the water-soluble unsaturated monomer. The aqueous solution of the water-soluble unsaturated monomer was cooled down to 70° C.

The resultant aqueous solution was put in a stainless container (250 mm×250 mm×30 mm) and exposed to UV radiation (exposure dose: 10 mW/cm$^2$) to conduct a UV polymerization for 90 seconds and obtain a hydrogel polymer. The hydrogel polymer thus obtained was milled to a size of 2 mm×2 mm and measured in regards to the moisture content, which was 40.1%.

The hydrogel polymer was spread on a stainless wire gauze having a hole size of 600 μm to a thickness of about 30 mm and dried in a hot air oven at 160° C. for 5 hours. The dried polymer was milled by using a milling machine and then size-distributed through a standard sieve according to the ASTM standards to obtain a base resin having a particle size of 150 to 850 μm and a fine powder having a particle diameter of less than 150 μm. The yield of the fine powder was 15 wt. % with respect to the dried polymer.

The base resin had a centrifuge retention capacity of 37.4 g/g and a water-soluble component content of 7.7%.

Preparation Example 8

500 g of acrylic acid, 0.675 g of 1.6-hexadiol diacrylate (HDDA) and 0.2 g of diphenyl (2,4,6-trimethylbenzoyl)-phosphine oxide were dissolved in a 3 L-glass container equipped with a stirrer, a nitrogen feeder, and a thermocouple. Then, 896.4 g of 24.5% sodium hydroxide solution was added while nitrogen is continuously fed, to prepare an aqueous solution of the water-soluble unsaturated monomer. The aqueous solution of the water-soluble unsaturated monomer was cooled down to 50° C.

The resultant aqueous solution was put in a stainless container (250 mm×250 mm×30 mm) and exposed to UV radiation (exposure dose: 10 mW/cm$^2$) to conduct a UV polymerization for 90 seconds and obtain a hydrogel polymer. The hydrogel polymer thus obtained was milled to a size of 2 mm×2 mm and measured in regards to the moisture content, which was 39.8%.

The hydrogel polymer was spread on a stainless wire gauze having a hole size of 600 μm to a thickness of about 30 mm and dried in a hot air oven at 170° C. for 5 hours. The dried polymer was milled by using a milling machine and then size-distributed through a standard sieve according to the ASTM standards to obtain a base resin having a particle size of 150 to 850 μm and a fine powder having a particle diameter of less than 150 μm. The yield of the fine powder was 15 wt. % with respect to the dried polymer.

The base resin had a centrifuge retention capacity of 39.2 g/g and a water-soluble component content of 16.2%.

Example 1

The base resin obtained in the preparation example 2 was used as a second polymer. 1 g of the second polymer was mixed with a crosslinking solution containing 1.0 g of ethylene carbonate, 4.0 g of water, 0.3 g of oxalic acid and 0.02 g of silica. The resultant mixture was uniformly mixed with 100 g of the base resin obtained in the preparation example 1 (i.e., a first polymer) and then dried in a hot air oven at 160° C. for 60 minutes for a reaction. The dried powder was size-distributed through a standard sieve according to the ASTM standards to yield the final SAP having a particle size of 150 to 850 μm.

Example 2

The procedures were performed in the same manner as described in the example 1, excepting that the final SAP was prepared using the base resin obtained in the preparation example 3 as the first polymer and the base resin obtained in the preparation example 4 as the second polymer.

Example 3

The procedures were performed in the same manner as described in the example 1, excepting that the final SAP was prepared using the base resin obtained in the preparation example 5 as the first polymer and the base resin obtained in the preparation example 6 as the second polymer.

Example 4

The procedures were performed in the same manner as described in the example 1, excepting that the final SAP was prepared using the base resin obtained in the preparation example 7 as the first polymer and the base resin obtained in the preparation example 8 as the second polymer.

Example 5

The procedures were performed in the same manner as described in the example 1, excepting that the final SAP was prepared using the base resin obtained in the preparation example 1 as the first polymer and the base resin obtained in the preparation example 6 as the second polymer.

Example 6

The procedures were performed in the same manner as described in the example 1, excepting that the final SAP was prepared using the base resin obtained in the preparation example 5 as the first polymer and the base resin obtained in the preparation example 2 as the second polymer.

Example 7

The procedures were performed in the same manner as described in the example 1, excepting that the final SAP was prepared using the base resin obtained in the preparation example 3 as the first polymer and the base resin obtained in the preparation example 1 as the second polymer.

Example 8

The procedures were performed in the same manner as described in the example 1, excepting that the final SAP was prepared using the base resin obtained in the preparation example 7 as the first polymer and the base resin obtained in the preparation example 5 as the second polymer.

Example 9

The procedures were performed in the same manner as described in the example 1, excepting that the final SAP was prepared using the base resin obtained in the preparation example 4 as the first polymer and the base resin obtained in the preparation example 2 as the second polymer.

Example 10

The procedures were performed in the same manner as described in the example 1, excepting that the final SAP was prepared using the base resin obtained in the preparation example 6 as the first polymer and the base resin obtained in the preparation example 8 as the second polymer.

Example 11

The procedures were performed in the same manner as described in the example 1, excepting that the final SAP was prepared using the base resin obtained in the preparation example 1 as the first polymer and the base resin obtained in the preparation example 8 as the second polymer.

Example 12

The procedures were performed in the same manner as described in the example 1, excepting that the final SAP was prepared using the base resin obtained in the preparation example 5 as the first polymer and the base resin obtained in the preparation example 8 as the second polymer.

Example 13

The procedures were performed in the same manner as described in the example 1, excepting that the final SAP was prepared using 2.0 g of ethylene glycol in place of 1.0 g of ethylene carbonate as the crosslinking agent.

Example 14

The procedures were performed in the same manner as described in the example 1, excepting that the final SAP was prepared using 2.0 g of propanediol in place of 1.0 g of ethylene carbonate as the crosslinking agent.

Example 15

The procedures were performed in the same manner as described in the example 1, excepting that the final SAP was prepared using 1.5 g of propanediol and 0.5 g of ethylene glycol in place of 1.0 g of ethylene carbonate as the crosslinking agent.

Example 16

The procedures were performed in the same manner as described in the example 1, excepting that the final SAP was prepared using 0.5 g of ethylene carbonate and 1.0 g of propanediol in place of 1.0 g of ethylene carbonate as the crosslinking agent.

Comparative Example 1

1 g of the base resin obtained in the preparation example 1 was mixed with 1.0 g of ethylene carbonate, 4.0 g of water, 0.3 g of oxalic acid and 0.02 g of silica. The resultant mixture was dried in a hot air oven at 160° C. for 60 minutes for a reaction. The dried powder was size-distributed through a standard sieve according to the ASTM standards to yield the final SAP having a particle size of 150 to 850 μm.

Comparative Example 2

The procedures were performed in the same manner as described in the comparative example 1, excepting that the final SAP was prepared using the base resin obtained in the preparation example 3.

Comparative Example 3

The procedures were performed in the same manner as described in the comparative example 1, excepting that the final SAP was prepared using the base resin obtained in the preparation example 5.

Comparative Example 4

The procedures were performed in the same manner as described in the comparative example 1, excepting that the final SAP was prepared using the base resin obtained in the preparation example 7.

TABLE 1

|  | First polymer | Second polymer | Crosslinking agent |
| --- | --- | --- | --- |
| Example 1 | Preparation Example 1 | Preparation Example 2 | Ethylene carbonate |
| Example 2 | Preparation Example 3 | Preparation Example 4 | Ethylene carbonate |
| Example 3 | Preparation Example 5 | Preparation Example 6 | Ethylene carbonate |
| Example 4 | Preparation Example 7 | Preparation Example 8 | Ethylene carbonate |
| Example 5 | Preparation Example 1 | Preparation Example 6 | Ethylene carbonate |
| Example 6 | Preparation Example 5 | Preparation Example 2 | Ethylene carbonate |
| Example 7 | Preparation Example 3 | Preparation Example 1 | Ethylene carbonate |
| Example 8 | Preparation Example 7 | Preparation Example 5 | Ethylene carbonate |
| Example 9 | Preparation Example 4 | Preparation Example 2 | Ethylene carbonate |
| Example 10 | Preparation Example 6 | Preparation Example 8 | Ethylene carbonate |
| Example 11 | Preparation Example 1 | Preparation Example 3 | Ethylene carbonate |
| Example 12 | Preparation Example 5 | Preparation Example 7 | Ethylene carbonate |

TABLE 1-continued

|  | First polymer | Second polymer | Crosslinking agent |
|---|---|---|---|
| Example 13 | Preparation Example 1 | Preparation Example 2 | Ethylene glycol |
| Example 14 | Preparation Example 1 | Preparation Example 2 | 1,3-propanediol |
| Example 15 | Preparation Example 1 | Preparation Example 2 | Ethylene glycol + 1,3-propanediol |
| Example 16 | Preparation Example 1 | Preparation Example 2 | Ethylene carbonate + 1,3-propanediol |
| Comparative Example 1 | Preparation Example 1 | — | Ethylene carbonate |
| Comparative Example 2 | Preparation Example 3 | — | Ethylene carbonate |
| Comparative Example 3 | Preparation Example 5 | — | Ethylene carbonate |
| Comparative Example 4 | Preparation Example 7 | — | Ethylene carbonate |

EXPERIMENTAL EXAMPLES

<Measurement of Properties of SAP>

Centrifuge Retention Capacity

The centrifuge retention capacity was measured according to the EDANA WSP 241.2 method. 0.2 g of the sample was put in a tea bag, which is sealed airtight and dipped in a 0.9% saline water solution for 30 minutes. In order to measure the centrifuge retention capacity, the soaked tea bag was put into a centrifugal separator at 250 G, dehydrated for 30 minutes and then weighed to measure the amount of the saline water retained by the SAP.

Absorption Under Pressure

The absorption under pressure was measured according to the EDANA WSP 242.2 method. 0.9 g of the sample was uniformly size-distributed into a measuring cylinder and pressed under the pressure of 49.2 g/cm$^2$ (0.7 psi) by using a piston and a weight. The sample was transferred to a schale containing a 0.9% saline water solution to absorb the solution for 60 minutes. The increased weight after 60 minutes was divided by the weight of the sample to calculate the absorption under pressure.

Permeability

The permeability was measured by using a 0.9% saline water solution under the load of 0.3 psi according to the method disclosed in the literature (Buchholz, F. L. and Graham, A. T., "Modern Superabsorbent Polymer Technology," John Wiley & Sons(1998), page 161).

0.2 g of the sample was put in a cylinder and then mixed with 50 g of a 0.9% saline water solution. After 30 minutes, the weight of 0.3 psi was loaded on the sample absorbing the 0.9% saline water solution and kept still for one minute. Subsequently, the stopcock under the cylinder was open to measure the time taken until the 0.9% saline water solution passes from the marked upper limit line down to the marked lower limit line. All the measurements were carried out at the temperature of 24±1° C. and the relative humidity of 50±10%.

The passage time from the upper limit line to the lower limit line was measured for every sample and the passage time without the SAP was measured as given by the following equation 1:

Permeability(sec)=Time(sample)−Time(without SAP)  [Equation 1]

The final SAPs of Examples 1 to 16 and Comparative Examples 1 to 4 were measured in regards to the properties. The measurement results are presented in Table 2.

TABLE 2

|  | Properties | | |
|---|---|---|---|
|  | Centrifuge retention capacity (g/g) | Absorption under pressure 0.7 psi (g/g) | Permeability (sec) |
| Example 1 | 32.6 | 24.5 | 87 |
| Example 2 | 30.1 | 24.6 | 48 |
| Example 3 | 32.6 | 24.5 | 86 |
| Example 4 | 31.0 | 24.3 | 51 |
| Example 5 | 33.1 | 24.3 | 84 |
| Example 6 | 32.9 | 24.5 | 79 |
| Example 7 | 30.2 | 25.6 | 52 |
| Example 8 | 30.3 | 25.7 | 55 |
| Example 9 | 30.5 | 25.1 | 56 |
| Example 10 | 31.2 | 24.9 | 67 |
| Example 11 | 32.1 | 24.7 | 72 |
| Example 12 | 32.7 | 24.2 | 83 |
| Example 13 | 32.4 | 24.6 | 73 |
| Example 14 | 33.0 | 24.7 | 88 |
| Example 15 | 32.8 | 25.1 | 82 |
| Example 16 | 33.0 | 25.2 | 88 |
| Comparative Example 1 | 33.5 | 23.9 | 185 |
| Comparative Example 2 | 30.5 | 24.9 | 152 |
| Comparative Example 3 | 33.4 | 23.6 | 176 |
| Comparative Example 4 | 32.2 | 23.8 | 163 |

Referring to Table 2, the SAPs prepared by the method of the present invention have good properties irrespective of the method for initializing polymerization or the properties of the first and second polymers. In particular, while the general SAPs with high permeability tend to have low centrifuge retention capacity and low absorption under pressure, the SAPs of the present invention can have high permeability without deterioration in the centrifuge retention capacity and the absorption under pressure. Contrarily, the SAPs prepared by the crosslinking reaction with a crosslinking agent in the form of an aqueous solution according to the general method as in the comparative examples 1 to 4 are inferior in liquid-penetrating properties to the SAPs of the examples of the present invention.

What is claimed is:

1. A method of preparing a super absorbent polymer, comprising:
   preparing a first polymer by carrying out a thermal polymerization or photo polymerization of a monomer composition comprising a water-soluble ethylene-based unsaturated monomer and a polymerization initiator;
   preparing a second polymer by carrying out a thermal polymerization or photo polymerization of a monomer composition comprising a water-soluble ethylene-based unsaturated monomer and a polymerization initiator;
   drying the first polymer;
   milling the dried first polymer; and
   mixing the milled first polymer with the second polymer in the free swelling state using the crosslinking solution to cause a crosslinking reaction of the first and second polymers.

2. The method as claimed in claim 1, wherein the crosslinking solution comprises water and a crosslinking agent.

3. The method as claimed in claim 2, wherein the crosslinking agent comprises at least one selected from the group consisting of a polyhydric alcohol compound; an epoxy compound; a polyamine compound; a haloepoxy compound; a condensation product of a halogepoxy compound; an oxazoline compound; a mono-, di-, or poly-oxazolidinone compound; a cyclic urea compound; a polyvalent metal salt; and an alkylene carbonate compound.

4. The method as claimed in claim 2, wherein the content of the crosslinking agent is 0.01 to 3 parts by weight with respect to 100 parts by weight of the first and second polymers in total.

5. The method as claimed in claim 2, wherein the weight ratio of the crosslinking agent to water in the crosslinking solution is 1:1 to 1:10.

6. The method as claimed in claim 1, wherein the second polymer is free-swollen with the crosslinking solution having a weight 0.5 to 500 times greater than the total weight of the second polymer.

7. The method as claimed in claim 1, wherein 1 to 20 parts by weight of the second polymer free-swollen with the crosslinking solution is mixed with 100 parts by weight of the first polymer to cause a crosslinking reaction.

8. The method as claimed in claim 1, wherein in the step of carrying out a crosslinking reaction, the crosslinking reaction is carried out at a temperature of 100 to 250° C.

9. The method as claimed in claim 1, further comprising:
   size-distributing the milled first polymer, after the step of milling the dried first polymer.

10. The method as claimed in claim 1, wherein the super absorbent polymer has a centrifuge retention capacity of 20 to 55 g/g as measured according to the EDANA WSP 241.2.

\* \* \* \* \*